United States Patent [19]

Mrozik

[11] 4,427,663

[45] Jan. 24, 1984

[54] 4″-KETO-AND 4″-AMINO-4″-DEOXY AVERMECTIN COMPOUNDS AND SUBSTITUTED AMINO DERIVATIVES THEREOF

[75] Inventor: Helmut H. Mrozik, Matawan, N.J.

[73] Assignee: Merck & Co., Inc., Rahway, N.J.

[21] Appl. No.: 358,736

[22] Filed: Mar. 16, 1982

[51] Int. Cl.³ .................... A61K 31/71; C07H 15/22
[52] U.S. Cl. .................................. 424/180; 536/7.1; 424/181
[58] Field of Search ................... 424/180; 536/7.1

[56] References Cited

U.S. PATENT DOCUMENTS

| | | | |
|---|---|---|---|
| 4,044,123 | 8/1977 | Daniels et al. | 536/13.6 |
| 4,085,119 | 4/1978 | Myers . | |
| 4,090,017 | 5/1978 | Sciavolino . | |
| 4,098,993 | 7/1978 | Bright . | |
| 4,107,435 | 8/1978 | Ross | 536/13.6 |
| 4,133,950 | 1/1979 | Myers . | |
| 4,199,569 | 4/1980 | Chabala et al. . | |
| 4,206,205 | 6/1980 | Mrozik et al. . | |
| 4,310,519 | 1/1982 | Albers-Schonberg et al. . | |

OTHER PUBLICATIONS

*Chemical Abstracts* 91: 175223f to Bright (II).
*Chemical Abstracts* 90: 23614a to Sciavolino (II).
*Chemical Abstracts* 90: 23615b to Sciavolino (III).

*Primary Examiner*—Johnnie R. Brown
*Attorney, Agent, or Firm*—David L. Rose; Mario A. Monsoo

[57] ABSTRACT

There are disclosed novel avermectin compounds wherein the 4″ hydroxy group is oxidized to a keto group or replaced with an amino or substituted amino group. The keto compounds are prepared by oxidation with reagents such as oxalyl chloride in dimethylsulfoxide. The amino compounds are prepared from the ketone using a reducing agent and an aminating agent. Substituted amino compounds are prepared from the thus produced unsubstituted amino compounds. The keto compounds and amino compounds have utility as anti-parasitic agents and compositions for that use are also disclosed. The compounds are also highly potent insecticides against agricultural pests. In addition the amino compounds have anti-bacterial activity which is not found in any of the precursors.

14 Claims, No Drawings

4"-KETO-AND 4"-AMINO-4"-DEOXY AVERMECTIN COMPOUNDS AND SUBSTITUTED AMINO DERIVATIVES THEREOF

BACKGROUND OF THE INVENTION

The term avermectin (previously referred to as C-076) is used to describe a series of compounds isolated from the fermentation broth of an avermectin producing strain of *Streptomyces avermitilis* and derivatives thereof. The morphological characteristics of the culture are completely described in U.S. Pat. No. 4,310,519. The avermectin compounds are a series of macrolides, each of which is substituted thereon at the 13-position with a 4-(α-L-oleandrosyl)-α-L-oleandrose group. The avermectin compounds and the instant derivatives thereof have a very high degree of anthelmintic and anti-parasitic activity.

The avermectin series of compounds isolated from the fermentation broth have the following structure:

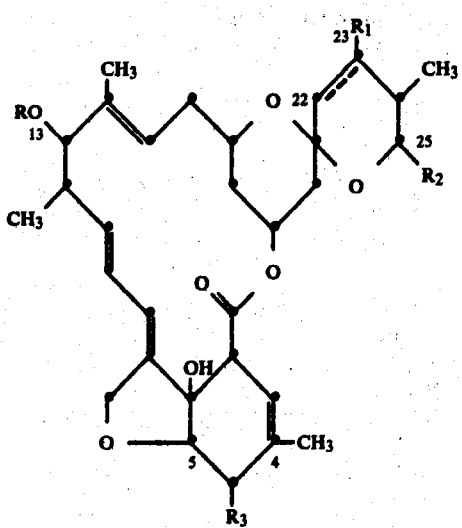

wherein R is the 4'-(α-1-oleandrosyl)-α-1-oleandrose group of the structure:

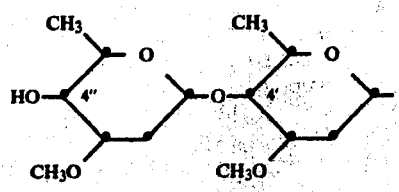

and wherein the broken line indicates a single or a double bond; $R_1$ is hydroxy and is present only when said broken line indicates a single bond;

$R_2$ is iso-propyl or sec-butyl; and $R_3$ is methoxy or hydroxy.

There are eight different avermectin natural product compounds and they are given the designations A1a, A1b, A2a, A2b, B1a, B1b, and B2a based upon the structure of the individual compounds.

In the foregoing structural formula, the individual avermectin compounds are as set forth below. (The R group is 4'(α-L-oleandrosyl)-α-L-oleandrose):

| | | | |
|---|---|---|---|
| A1a | Double Bond | sec-butyl | —OCH$_3$ |
| A1b | Double Bond | iso-propyl | —OCH$_3$ |
| A2a | —OH | sec-butyl | —OCH$_3$ |
| A2B | —OH | iso-propyl | —OCH$_3$ |
| B1a | Double Bond | sec-butyl | —OH |
| B1b | Double Bond | iso-propyl | —OH |
| B2a | —OH | sec-butyl | —OH |
| B2b | —OH | iso-propyl | —OH |

The avermectin compounds are generally isolated as mixtures of a and b components. Such compounds differ only in the nature of the $R_2$ substituent and the minor structural differences have been found to have very little effect on the isolation procedures, chemical reactivity and biological activity of such compounds.

The end hydroxy group of the disaccharide substituent at the 13-position is situated at what is referred to as the 4"-position. The reactions and substitutions at the 4"-position is the subject matter of this invention.

SUMMARY OF THE INVENTION

The instant invention is concerned with certain derivatives of avermectin compounds wherein the 4"-hydroxy group is oxidized to ketone and replaced by an amino or substituted amino group. Thus it is an object of the instant invention to describe such 4"-substituted avermectin compounds. A further object is to describe processes for the preparation of such compounds. A still further object is to describe the uses of such compounds as anti-parasitic agents and anti-bacterial agents. Still further objects will become apparent from a reading of the following description.

DESCRIPTION OF THE INVENTION

The compounds of the instant invention have the following structural formula.

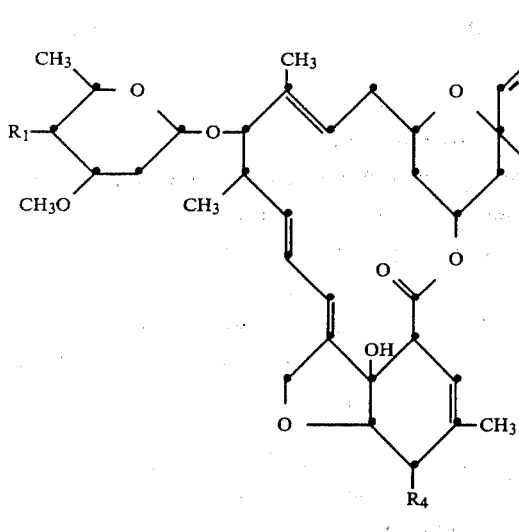

wherein $R_1$ is =O, —$NR_5R_6$ or

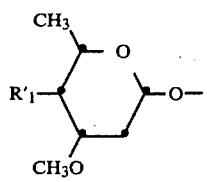

wherein
$R'_1$ is =O, or —$NR_5R_6$;
$R_5$ and $R_6$ are independently hydrogen, loweralkyl, loweralkanoyl, substituted benzenesulfonyl wherein the substitutent is halogen or loweralkyl sulfonyl;
$R_2$ is hydrogen or hydroxy,
$R_2$ is iso-propyl or sec-butyl,
$R_4$ is hydroxy or methoxy,
and the broken line indicates a single or a double bond at the 22,23-position, provided that $R_2$ is hydroxy only when the broken line indicates a single bond.

The term "loweralkyl" when used in the instant application is intended to represent those alkyl groups either straight or branched chain which have from 1–5 carbon atoms. Examples of such alkyl groups are methyl, ethyl, propyl, iso-propyl, butyl, sec-butyl, pentyl, and the like.

The term "loweralkanoyl" is intended to include those alkanoyl groups containing from one to five carbon atoms in either a straight or branched chain. Examples of such alkanoyl groups are formyl, acetyl, propenyl, butyryl, valeryl, and the like.

The term "halogen" is intended to include those halogen atoms fluorine, chlorine, bromine and iodine.

One aspect of the preferred compounds of this invention is realized in the above structural formula when $R_1$ is

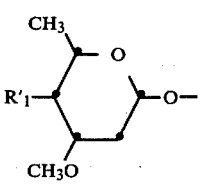

and $R'_1$ is =O or $NR_5R_6$ and $R_5$ and $R_6$ are independently hydrogen, methyl or acetyl. Further, examples of preferred compounds of the instant invention are:
4"-keto avermectin B1a;
4"-keto avermectin B1b;
4"-keto-22,23-dihydro avermectin B1a;
4"-keto-22,23-dihydro avermectin B1b;
4"-deoxy-4"-amino avermectin B1a;
4"-deoxy-4"-amino avermectin B2b;
4"-deoxy-4"-amino-22,23-dihydro avermectin B1a;
4"-deoxy-4"-amino-22,23-dihydro avermectin B1b;
4"-deoxy-4"-acetylamino avermectin B1a;
4"-deoxy-4"-acetylamino avermectin B1b;
4"-deoxy-4"-acetylamino-22,23-dihydro avermectin B1a;
4"-deoxy-4"-acetylamino-22,23-dihydro avermectin B1b;
4"-deoxy-4"-dimethylamino avermectin B1a;
4"-deoxy-4"-dimethylamino avermectin B1b;
4"-deoxy-4"-dimethylamino-22,23-dihydro avermectin B1a;
4"-deoxy-4"-dimethylamino-22,23-dihydro avermectin B1b;
4"-deoxy-4"-p-chloro benzenesulfonylamino-22,23-dihydro avermectin B1a;
4"-deoxy-4"-p-chloro benzenesulfonylamino-22,23-dihydro avermectin B1b;
4"-deoxy-4"-(2-methylbenzenesulfonylamino)avermectin B1a;
4"-deoxy-4"-(2-methylbenzenesulfonylamino)avermectin B1b.

The "b" compounds, those with a 25-iso-propyl group, are very difficult to separate from the corresponding "a" compound with a 25-sec-butyl group and as such the compounds are generally isolated as mixtures of the two compounds. Thus references in the instant application to "a" compounds such as B1a, A1a, and the like, are construed to actually contain a certain proportion of the corresponding "b" compound. Alternatively, this representation of a mixture is sometimes done by referring to the B1 or B2 compounds or by separating the "a" compound from the "b" compound by a slash (/) such as B1a/B1b, B2a/B2b and the like.

The compounds of the instant invention are prepared using the procedure exemplified in the following reaction scheme:

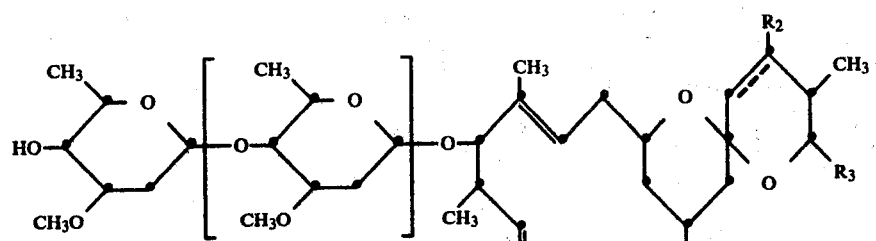
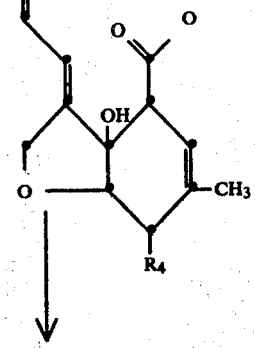
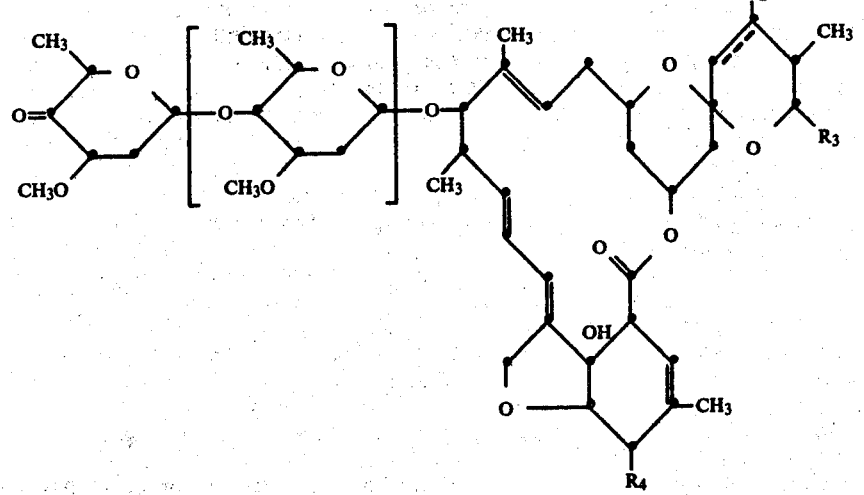
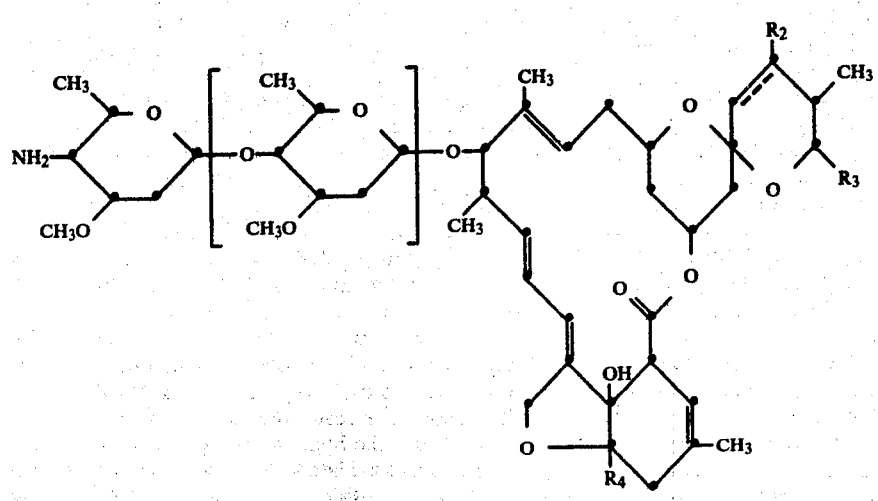

-continued

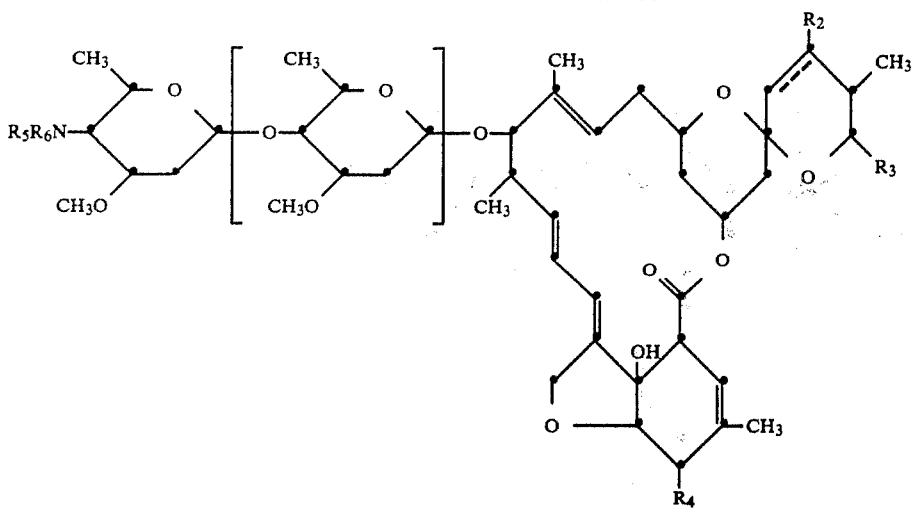

wherein $R_2$, $R_3$ and $R_4$ are as previously defined and the brackets indicate that the saccharide group contained therein may be either present or absent in the molecule.

In the first step of the foregoing reaction scheme, the avermectin starting materials which may be either the naturally occuring products, the 22,23-dihydro derivatives thereof or the monosaccharide derivative thereof, are oxidized at the 4''-position to the corresponding keto compound. During the procedure the presence of any hydroxy groups at the 5 and 23-position will require that such hydroxy groups be protected in order that they too are not oxidized. The 7-hydroxy group is very non-reactive and inert and need not be protected. The procedure used to prepare the protected intermediates are described below. The oxidation reaction is carried out in an inert solvent such as methylene chloride using oxalyl chloride or trifluoroacetic anhydride in dimethylsulfoxide as the oxidizing agent. Additionally N-chlorosuccinimide in dimethylsulfide may be employed. The reaction proceeds by dissolving the oxalyl chloride or trifluoroacetic anhydride and dimethylsulfoxide (or other oxidizing reagents) in methylene chloride and cooling to from $-50°$ to $-80°$ C. and adding dropwise a methylene chloride solution of the avermectin compound to be oxidized. The addition is carried out over a period of from 15 minutes to 1 hour and then triethylamine is added dropwise over a period of from 1 to 15 minutes. The reaction mixture is then allowed to warm to room temperature over a period of from ½ to 1 hour. The 4''-keto compound is isolated using techniques known to those skilled in the art.

In the next step, the 4''-keto compound is aminated to prepare the unsubstituted amino compound ($R_5 = R_6 =$ hydrogen). The reaction is carried out in an inert solvent such as methanol at from $-25°$ to $+10°$ C. using ammonium salts and sodium cyanoborohydride as the aminating and reducing reagents. The reaction is complete in from 15 minutes to 2 hours and the product 4''-deoxy-4''-amino compound is isolated using techniques known to those skilled in the art. Suitable ammonium salts are the acetate, propionate, benzoate and the like. The acetate is preferred.

As a variation to the foregoing animation reaction, methyl ammonium salts could be used in place of the ammonium salts to prepare the monomethyl substituted compound directly. The same reagents, salts and reaction conditions as described above can be used for such a reaction.

The substitution reaction wherein the substituent is an acyl function is carried out using an acylating reagent in the presence of a base in an inert solvent. The preferred acylating reagents are loweralkanoyl anhydrides, loweralkanoyl halides, substituted benzene sulfonyl chlorides, lower alkyl sulfonyl chlorides, and the like. The reaction is carried out in an inert solvent such as methylene chloride in the presence of a non-reactive base such as pyridine or triethylamine in order to neutralize the acid produced during the course of the reaction. The reaction temperature is from $-10°$ to $25°$ C. and the reaction is complete in from 5 minutes to 1 hour. The product is isolated using known techniques.

The reaction for the preparation of the 4''-deoxy-4''-dialkylamino compounds is carried out using the alkylating reaction conditions of formaldehyde and a reducing agent such as sodium borohydride, in methanol. The reaction is carried out in aqueous medium using excess aqueous formaldehyde along with the presence of a small amount of acid such as acetic acid to facilitate the reaction. The reaction is carried out at from $-10°$ to $+10°$ C. with the solution of the avermectin compound in methanol added dropwise over a period of from 30 to 60 minutes to the alkylating reagent mixture and the product is isolated using known techniques.

PREPARATION OF STARTING MATERIALS

Th ultimate starting materials for the compounds of this invention are the avermectin fermentation products defined above. Thus it is apparent that additional reactions are required to prepare the instant compounds. Specifically, reactions are carried out at the 5, 13, 22, and 23-positions. It is generally preferred to prepare whatever substituents are required at these positions before the oxidation at the 4''-hydroxy and subsequent substitution on the thus produced 4''-keto. Such a procedure generally avoids undesirable side reactions. This technique is not required, however, and if desired other sequences may be used. In addition, during the oxidation and substitution reaction described above, it is necessary to protect the hydroxy groups at the 5- and 23-positions to avoid oxidation or substitution at such positions. With these positions protected the reactions may be carried out at the 4-position without affecting the remainder of the molecule. Subsequent to any of the above described reactions the protecting group may be removed and the unprotected product isolated. The protecting group employed is ideally one which may be readily synthesized, will not be affected by the reactions at the 4"-position and may be readily removed without affecting any other functions of the molecule. One preferred type of protecting group for the avermectin type of molecule is the tri-substituted silyl group, preferably the trialkyl silyl group. One especially preferred example, is the t-butyl dimethylsilyl group. The reaction preparing the protected compound is carried out by reacting the hydroxy compound with the appropriately substituted silylhalide, preferably the silylchloride in an aprotic polar solvent such as dimethylformamide. Imidazole is added as a catalyst. The reaction is complete in from 1 to 24 hours and at from 0° to 25° C. For the 5-position hydroxy group the reaction is complete in from ½ to 3 hours at from 0° C. to room temperature. This reaction is selective to the 5 position under the conditions above described and very little, if any, silylation is observed at other hydroxy substituted positions. If it is desired to protect the 23-hydroxy group a 4", 5,23-tri(phenoxyacetyl) derivative can be prepared. Basic hydrolysis will leave the highly hindered 23-O-substituent but hydrolize the 5- and 4"-O-phenoxy acetyl groups. The 5-position is then protected as described above, selectively with t-butyldimethylsilyl.

The silyl group may be removed after the other contemplated reactions may be carried out. The silyl group or groups are removed by stirring the silyl compound in methanol catalized by a catalytic amount of an acid preferably a sulfonic acid such as p-toluene sulfonic acid. The reaction is complete in about 1 to 12 hours at from 0° to 50° C.

Another of the starting materials used in the foregoing reaction scheme are those in which the 22,23 double bond of the "1" type compounds has been reduced to a single bond. As is readily apparent from an analysis of the structure of avermectin starting materials there are 5 unsaturations in the 1-series of compounds. Thus in the one series of compounds it is necessary to reduce the 22,23 double bond while not affecting the remaining four unsaturations or any other functional group present on the molecule in order to selectively prepare the 22,23 dihydro avermectins. It is necessary to select a specific catalyst for the hydrogenation, one that will selectively hydrogenate the least hindered from among a series of unsaturations. The preferred catalyst for such a selective hydrogenation procedure is one having the formula:

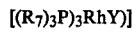

[(R$_7$)$_3$P)$_3$RhY)]

wherein R$_7$ is loweralkyl, phenyl or loweralkyl substituted phenyl and Y is halogen. The reduction procedure is completely described in U.S. Pat. No. 4,199,569.

The other starting materials which are used in the above reaction scheme involve the preparation of the mono-saccharide compound. That is those compounds wherein one of the α-1-oleandrosyl groups have been removed. The removal of the terminal α-1-oleandrose leaves a hydroxy group at the 4'-position which is equally amenable to the reactions described in the foregoing reaction scheme. Of course in such a case the products prepared are 4'-keto and 4'-deoxy 4'-amino derivatives rather than the 4"-keto and 4"-deoxy 4"-amino derivatives. The processes which may be used to prepare the monosaccharide derivatives of the avermectin compounds are described in U.S. Pat. No. 4,206,205. The reaction consists generally of treating the starting material disaccharide with acid in an aqueous organic solvent mixture. Water concentrations of from 0.1 to 20% by volume and acid concentrations of from about 0.01 to 0.1% will predominantly produce the monosaccharide product.

A further procedure for the preparation of the monosaccharide utilizes a 1% mineral acid solution in isopropanol at for 20°–40° C. preferably at room temperature for from 6 to 24 hours. Mineral acids such as sulfuric, hydrohalic, phosphoric and the like may be employed.

The novel compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia and Oesphagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The substituted avermectin compounds of this invention have unexpectedly high activity against these parasites, and in addition are also active against Dirofilaria in dogs, Namatospiroides, Syphacia, Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasties of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica*.

The compounds are also useful against insect pests of stored grains such as Tribolium sp., Tenebrio sp. and of agricultural plants such as spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture. The compoundss are active against other plant pests such as the southern army worm and Mexican bean beetle larvae.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the avermectin derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1–5 days. With the preferred compounds of the invention, excellent control of such parasties is obtained in animals by administering from about 0.025 to 0.5 mg per kg of body weight in a single dose. Repeat treatments are given as required to combat re-infections and are dependent upon the species of parasite and the husbandry techniques being employed. The techniques for adminstering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active hydrogenated avermectin compounds are intimately dispersed throughout the carrier by methods such as grinding, stirring, milling or tumbling. Compositions containing from about 0.005 to 2.0% by weight of the active compound are particualrly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parastic diseases. Although the desired concentration of active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

The avermectin compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

In using the compounds of this invention, the individual substituted avermectin components may be prepared and used in that form. Alternatively, mixtures of two or more of the individual avermectin components may be used, as well as mixtures of the parent avermectin compounds, other avermectin compounds or other active compounds not related to avermectin, with the compounds of this invention.

The 4"-amino and substituted amino compounds of the present invention are valuable antibiotics active against various Gram-positive and Gram-negative bacteria and accordingly find utility in human and veterinary medicine. Representative pathogens which are sensitive to the instant compounds include: *Staphylococcus aureus, Escherichia coli, Klebsiella pneumoniae, Bacillus subtilis, Salmonella typhosa, Psuedomonas* and *Bacterium proteus*. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intravenously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrolidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter or other glycerides.

Composition for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalants, lozenges, or throat paints. For medication of the eyes or ears, the preparation may be presented in liquid or semi-solid form. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 0.1 to about 5 mg of active ingredient per kg. of body weight of the subject in one or more treatments per day. A preferred daily dosage for adult humans lies in the range of from about 0.1 to 20 mg. of active ingredient per kg. of body weight. Another factor influencing the precise dosage regimen, apart from the nature of the infection and peculiar identity of the individual being treated, is the molecular weight of the carbon species of this invention.

The compositions for human delivery per unit dosage, whether liquid or solid, may contain from 0.1% to 99% of active material, the preferred range being from about 10–60%. The composition will generally contain from about 5 mg. to about 50 mg. of the active ingredient; however, in general, it is preferable to employ a dosage amount in the range of from about 5 mg to 100 mg. In parenteral administration, the unit dosage is usually the pure compound I in sterile water solution or in the form of a soluble powder intended for solution.

In the isolation of the avermectin compounds, which serve as starting materials for the instant process, from the fermentation broth, the various avermectin compounds will be found to have been prepared in unequal amounts. In particular an "a" series compound will be prepared in a higher proportion than the corresponding "b" series compound. The difference between the "a" series and "b" series is constant throughout the avermectin compounds and consists of a sec-butyl group and an iso-propyl group respectively at the 25 position. This difference, of course, does not interfere with any of the instant reactions. In particular it may not be necessary to separate the "b" components from the related "a" component. Separation of these closely related compounds is generally not practiced since the "b" compound is present only in a very small percent by weight, and the structural difference has negligible effect on the reaction processes and biological activities.

In particular it has been found that the starting materials for the compounds of this invention are very often prepared in a ratio of about 80% avermectin B1a and A1a and 20% avermectin B1b or A1b. Thus the preferred composition of this invention is one which contains about 80% of the "a" component and 20% of the "b" component.

The following examples are provided in order that this invention might be more fully understood; they are not to be construed as limitative of the invention.

The substituted avermectin derivatives prepared in the following examples are generally isolated as amorphous solids and not as crystalline solids. They are thus characterized analytically using techniques such as mass spectrometry, nuclear magnetic resonance, and the like. Being amorphous, the compounds are not characterized by sharp melting points, however, the chromatographic and analytical methods employed indicate that the compounds are pure.

In the following examples, the various starting materials therefor are avermectin compounds or derivatives of avermectin compounds. The avermectin compounds and the preparation and isolation thereof from fermentation broths are described in U.S. Pat. No. 4,310,519 issued Jan. 12, 1982. The selective 22,23-dihydro derivatives of avermectin compounds are decribed in U.S. Pat. No. 4,199,569 issued Apr. 22, 1980. The monosaccharide derivatives of avermectin compounds are described in U.S. Pat. No. 4,206,205 issued Jan. 3, 1980.

EXAMPLE 1

5-O-t-butyl-dimethylsilyl-22,23-dihydro avermectin B1a/B1b 3 g of 22,23-dihydro avermectin B1a/B1b in 30 ml of dry dimethylformamide was combined with 1.4 g of imidazole and stirred at room temperature until all the materials had dissolved. Then 1.56 g of t-butyl-dimethylsilyl chloride was added and the reaction mixture stirred at room temperature for 70 minutes. The reaction mixture was diluted with 150 ml of ether, water was added and the layers were separated. The aqueous layer was extracted twice more with ether and the combined ether layers washed four times with water and once with saturated sodium chloride solution. The ether layer was dried over magnesium sulfate and concentrated to dryness in vacuo affording 4.2 g of a white foam. The foam is chromatographed on 135 g. of 70–230 mesh silica gel and eluted with 5% tetrahydrofuran in methylene chloride. 1.15 G of 4''-5-di-O-t-butyl-dimethylsilyl-22,23-dihydro avermectin B1a/B1b and 2.6 g of 5-O-t-butyl dimethylsilyl-22,23-dihydro avermectin B1a/B1b were recovered as pure amorphous foams.

EXAMPLE 2

5-O-t-butyl-dimethylsilyl-4''-keto-22,23-dihydro-avmerectin B1a/B1b

In a dried flask purged with dry nitrogen was placed 97 μl of oxalyl chloride and 1.5 ml of methylene chloride. The reaction mixture was cooled to −60° C., 1 ml of the methylene chloride solution containing 160 μl of dimethylsulfoxide was added over a period of 3 minutes and the reaction mixture stirred at −60° C. for two minutes. 3 Ml of methylene chloride containing 500 mg of 5-O-t-butyl-dimethylsilyl 22,23-dihydro avermectin B1a/B1b was added dropwise over a period of 5 minutes and the reaction mixture stirred at room temperature for 30 minutes. At the end of this period, 0.71 ml of triethylamine was added dropwise and the reaction mixture was stirred at −60° C. for 5 minutes. The cold bath was removed and the reaction mixture was allowed to come to room temperature over a period of 45 minutes. 50 Ml of water was added and the reaction mixture was extracted 3 times with 40 ml of ether. The ether extracts were combined and washed 4 times with 20 ml of water, dried over magnesium sulfate and concentrated to dryness in vacuo affording 520 mg of a yellow glass. The yellow glass was dissolved in methylene chloride and placed on three 2,000μ silica gel preparative layer chromatography plates. The plates were developed with 10% ethyl acetate in methylenechloride and afforded 470 ml of yellow foam which was characterized by its 300 MHz nuclear magnetic resonance spectrum as 5-O-t-butyl-dimethylsilyl-4''-keto-22,23-dihydro avermectin B1a/B1b.

EXAMPLE 3

5-O-t-butyl-dimethylsilyl-4''-deoxy-4'''-amino-22,23-dihydro avermectin B1a/B1b

Into a dried flask was placed 200 mg of 5-O-t-butyl-dimethylsilyl-4''-keto-22,23-dihydro-avermectin B1a/B1b 2 ml of methanol, 160 mg of ammonium acetate and 12 mg of sodium cyanoborohydride. The reaction mixture was stopped and stirred at room temperature for 100 minutes. The reaction mixture was added to a 10 ml solution of saturated sodium carbonate diluted 1 to 1 with water to afford a gummy precipitate. The precipitate was extracted 4 times with 3 ml of ethyl acetate and the ethyl acetate layers were combined and washed four times with 1 ml of water. The organic layer was dried over magnesium sulfate and evaporated to dryness in a stream of nitrogen to afford 198 mg of yellow opaque glass. The glass was dissolved in methylene chloride and placed on three 1,000μ silica gel preparative layer chromatography plates and eluted with 7% methanol in methylene chloride to afford 19 mg of a yellow glass which was identified by 300 MHz nuclear magnetic resonance as 5-O-t-butyl-dimethylsilyl-4''-deoxy-4''-amino-22,23-dihydro avermectin B1a/B1b and 64 mg of a yellow glass which was identified by 300 MHz nuclear magnetic resonance as 5-O-t-butyl-dimethylsilyl-4''-deoxy-4''-epiamino-22,23-dihydro avermectin B1b/B1b.

EXAMPLE 4

4''-deoxy-4''-amino-22,23-dihydro-avermectin B1a/B1b 17 mg of 5-O t-butyl-dimethylsilyl -4''deoxy-4''-amino-22,23-dihydro avermectin B1a/B1b was dissolved in a few drops of methanol and cooled in an ice-bath with stirring. 3 ml of 1% (weight to volume), p-toluene sulfonic acid hydrate solution in methanol was added and the reaction mixture stirred for 55 minutes. The reaction mixture was added to dilute sodium bicarbonate solution and extracted 3 times with 3 ml portions of ethyl acetate. The organic layers were combined and washed 3 times with 1 ml of water and once with saturated sodium chloride solution. The organic layer was dried over magnesium sulfate and evaporated to dryness under a stream of nitrogen affording 18 mg of a yellow glass. The yellow glass was dissolved in methylene chloride and placed on a 250μ silica gel preparative layer chromatography plate and eluted with 8% methanol in methylene chloride. The band with an Rf of 0.20 afforded 8.5 mg of a white glass. Mass spectrometry and 300 MHz nuclear magnetic resonance identified it as 4''-deoxy-4''-amino-22,23-dihydro-avermectin B1a/B1b.

EXAMPLE 5

4''-deoxy-4''-epi-amino-22,23-dihydro avermectin B1a/B1b

Following the procedure of Example 4 using 60 mg of 5-O-t-butyl-dimethylsilyl 4''-deoxy-4'' epi-amino-22,23-dihydro avermectin B1a/B1b 6.0 ml of 1% weight to volume p-toluene sulfonic acid hydrate in methanol there was obtained 27.4 mg of 4''-deoxy-4''-epi-amino-22,23-dihydro avermectin B1a/B1b which structure was confirmed by mass spectrometry and 300 MHz nucelar magnetic resonance.

EXAMPLE 6

5-O-t-butyl-dimethylsilyl-4"-deoxy-4"-acetylamino 22,23-dihydro avermectin B1a/B1b 30 mg of 5-O-t-butyl-dimethylsilyl-4" deoxy-4" amino-22,23-dihydro avermectin B1a/B1b was combined with 0.5 ml of methylene chloride and cooled in an ice-bath. 6 Drops of pyridene was added followed by 2 Drops of acetic anhydride. The reaction mixture was stirred at 0° C. for 30 minutes. Water and ether were added, the layers were separated and the aqueous layer extracted again with ether. The organic layers were combined and washed four times with 1 ml portions of water, dried over magnesium sulfate and evaporated to dryness under a stream of nitrogen to afford 35 mg of a yellow glass. The yellow glass was dissolved in methylene chloride and placed on a 500μ silica gel preparative layer chromatography plate and eluted with a 1 to 1 mixture of ethyl acetate in methylene chloride to afford 14.6 mg of off-white foam. 300 MHz nuclear magnetic resonance characterized the material is 5-O-t-butyl-dimethylsilyl-4"-deoxy-4"-acetylamino-22,23-dihydro-avermectin B1a/B1b.

EXAMPLE 7

4"-deoxy-4"-acetylamino-22,23-dihydro avermectin B1a/B1b

Following the procedure of Example 4, 4"-acetylamino-4"-deoxy-5-O-t-butyldimethylsilyl-22,23-dihydroavermectin B1a/B1b was treated with a 1% solution of p-toluenesulfonic acid monohydrate in methanol (w/v) to give after isolation and purification 4"-acetylamino-4"-deoxy-22,23-dihydroavermectin B1a/B1b.

EXAMPLE 8

5-O-t-butyl-dimethylsilyl-4"-deoxy-4"-epi-acetylamino-22,23-dihydro-avermectin B1a/B1b Following the procedure of Example 6 wherein 5 mg of 5-O-t-butyl-dimethylsilyl-4"-deoxy-4"-epi-amino-22,23-dihydro avermectin B1a/B1b was employed, there was obtained 5-O-t-butyl-dimethylsilyl 4"-deoxy-4"-epi-acetylamino-22,23-dihydro avermectin B1a/B1b.

EXAMPLE 9

4"-deoxy-4"-epi-acetylamino-22,23-dihydro-avermectin B1a/B1b

Following the procedure of Example 4 in which 35 mg of 5-O-t-butyl-dimethylsilyl-4"-deoxy-4"-epi-acetylamino-22,23-dihydro avermectin B1a/B1b was employed with 4 ml of 1% weight to volume p-toluene sulfonic acid hydrate in methanol. There was obtained 19.4 mg of 4"-deoxy-4"-epi-acetylamino-22,23-dihydro-avermectin B1a/B1b.

EXAMPLE 10

4"-keto-22,23-dihydro-avermecting B1a/B1b 25 mg of 5-O-t-butyldimethylsilyl-4"-keto-22,23-dihydro-avermectin B1a/B1b in 3 mg of 1% weight to volume p-toluene sulfonic acid hydrate in methanol was stirred at room temperature for 20 minutes. 20 Ml of water was added and the reaction mixture extracted three times with 15 ml portions of ether. The ether layers were combined and washed three times with 3 ml portions of water dried over magnesium sulfate and evaporated to dryness in vacuo to afford 15 mg of a colorless glass. The glass was dissolved in methylene chloride and placed on a 1000μ silica gel preparative layer chromatography plate and eluted with 5% methanol in methylene chloride to afford 14.5 mg of an off-white glass characterized by mass spectrometry and 300 MHz nuclear magnetic resonance as 4"-keto 22,23-dihydro-avermectin B1a/B1b.

EXAMPLE 11

5-O-t-butyldimethylsilyl-4"-deoxy-4"-epi-N,N-dimethylamino-22,23-dihydro avermectin B1a/B1b 50 mg of 5-O-t-butyl-dimethylsilyl-4"-deoxy-4"-epi-amino-22,23-dihydro-avermectin B1a/B1b was dissolved in 0.7 ml of methanol and 0.4 ml of acetic acid added followed by 0.5 ml of 37% aqueous formaldehyde solution. The reaction mixture was stirred at room temperature for 30 minutes, cooled in an ice bath and 130 mg of sodium borohydride was added in 5–10 mg portions with 5–10 minutes separating each portion. Vigorous foaming accompanied each addition. A saturated sodium bicarbonate solution was added in small portions to the reaction mixture to neutrality followed by extraction with ether. The aqueous layer was extracted twice more with 20 ml portions of ether. The ether layers were combined and washed four times with 4 ml portions of water. The combined organic layers were dried over magnesium sulfate and evaporated to dryness in vacuo affording 40 ml of a slightly yellow glass. The glass was dissolved in methylene chloride and placed on a 1000μ silica gel preparative layer chromatography plate and developed with ethyl acetate to afford 30.5 mg of yellow glass identified by mass spectrometry as 5-O-t-butyldimethylsilyl-4"-deoxy-4"-epi-N,N-dimethylamino-22,23-dihydro avermectin B1a/B1b.

EXAMPLE 12

4"-deoxy-4"-epi-N,N-dimethylamino-22,23-dihydro-avermectin B1a/B1b

29 Mg of 5-O-t-butyl-dimethylsilyl-4"-deoxy-4"-epi-N,N-dimethylamino-22,23-dihydro avermectin B1a/B1b was treated with 3 ml of 1% weight to volume p-toluene sulfonic acid hydrate in methanol following the procedure of Example 4. There was afforded 15.8 mg of a white glass which was identified by mass spectrometry and 300 MHz nuclear magnetic resonance as 4"-deoxy-4"-epi-N,N-dimethylamino-22,23-dihydro-avermectin B1a/B1b.

EXAMPLE 13

5-O-t-Butyldimethylsilyl-4"-deoxy-4"-(4-chlorophenylsulfonylamino)-22,23-dihydroavermectin-B1a/B1b A solution of 100 mg of 5-O-t-butyldimethylsilyl-4"-deoxy-4"-amino-22,23-dihydroavermectin B1a/B1b is dissolved in 2 ml of methylenechloride and treated with 70 mg of triethylamine and 45 mg of 4-chlorobenzenesulfonylchloride at room temperature for 16 hrs. The usual work-up gives 5-O-t-butyldimethylsilyl-4"-deoxy-4"-(4-chlorophenylsulfonylamino)-22,23-dihydroavermectin-B1a/B1b in pure form.

EXAMPLE 14

4"-Deoxy-4"-(4-chlorophenylsulfonylamino)-22,23-dihydroavermectin-B1a/B1b

100 Mg of 5-O-t-butyldimethylsilyl-4"-deoxy-4"-(4-chlorophenylsulfonylamino)-22,23-dihydroavermectin-B1a/B1b is treated according to Example 4 with a solution of 1% of p-toluenesulfonic acid monohydrate in methanol for 30 min at room temperature affording 4''-deoxy-4''-(4-chlorophenylsulfonylamino)-22,23-dihydroavermectin-B1a/B1b in pure form.

EXAMPLE 15

4''-Keto-5-O-t-butyldimethylsilylavermectin-B1a/B1b

If avermectin B1a/B1b is reacted according to the procedures of Examples 1 and 2 4''-keto-5-O-t-butyldimethylsilylavermectin-B1a/B1b is obtained.

EXAMPLE 16

4''-Keto-avermectin-B1a/B1b

If the product of Example 15 is reacted according to the procedure of Example 10, 4''-ketoavermectin-B1a/B1b is obtained.

EXAMPLE 17

4''-Amino-4''-deoxyavermectin B1a/B1b

If the product of Example 15 is reacted according to the procedures of Examples 3 and 4 4''-amino-4''-deoxyavermectin B1a/B1b is obtained.

EXAMPLE 18

4''-Acetylamino-4''-deoxyavermectin B1a/B1b

If the product of Example 15 is reacted according to the procedures of Examples 3, 6 and 7 4''-acetylamino-4''-deoxavermectin B1a/B1b is obtained.

EXAMPLE 19

4'-Keto-5-O-t-butyldimethylsilyl-22,23-dihydroavermectin B1a/B1b monosaccharide

If 22,23-dihydroavermectin B1a/B1b-monosaccharide is reacted according to the procedures of Examples 1 and 2, 4'-keto-5-O-t-butyldimethylsilyl-22,23-dihydroavermectin B1a/B1b monosaccharide is obtained.

EXAMPLE 20

4'-Keto-22,23-dihydroavermectin B1a/B1b-monosaccharide

If the product of Example 19 is reacted according to the procedures of Example 10 4'-keto-22,23-dihydroavermectin B1a/B1b-monosaccharide is obtained.

EXAMPLE 21

4'-Amino-4'-deoxy-22,23-dihydroavermectin-B1a/B1b monosaccharide

If the product of Example 19 is reacted according to the procedures of Examples 3 and 4, 4'-amino-4'-deoxy-22,23-dihydroavermectin-B1a/B1b-monosaccharide is obtained.

EXAMPLE 22

4'-Acetylamino-4'-deoxy-22,23-dihydroavermectin-B1a/B1b-monosaccharide

If the product of Example 19 is reacted according to the procedures of Examples 3, 6 and 7, 4'-acetylamino-4'-deoxy-22,23-dihydroavermectin-B1a/B1b-monosaccharide is obtained.

What is claimed is:

1. A compound having the formula:

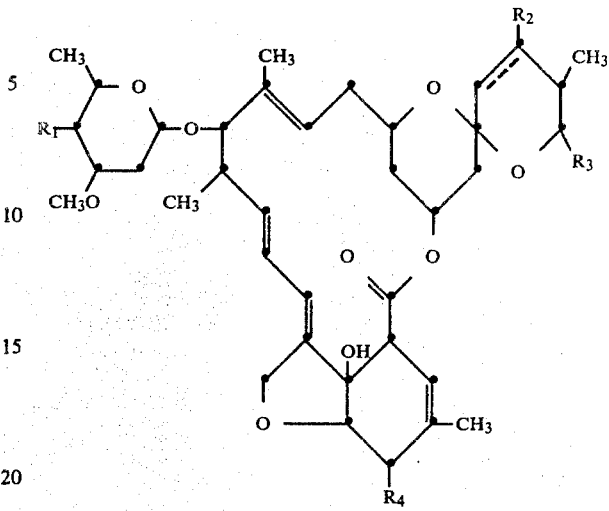

wherein $R_1$ is $=O$, $-NR_5R_6$ or

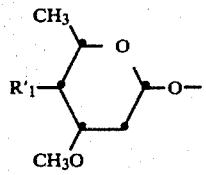

wherein
$R_1'$ is $=O$ or $-NR_5R_6$;
$R_5$ and $R_6$ are independently hydrogen, loweralkyl, loweralkanoyl, substituted benzenesulfonyl wherein the substituent is halogen; or loweralkyl sulfonyl;
$R_2$ is hydrogen or hydroxy;
$R_3$ is sec-butyl or iso-propyl;
$R_4$ is hydroxy or methoxy;
and the broken line indicates a single or a double bond at the 22,23-position provided that $R_2$ can only be hydroxy when the broken line indicates a single bond.

2. The compound of claim 1 wherein $R_1$ is:

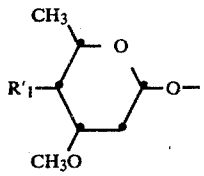

and $R'_1$ is $=O$, or $-NR_5R_6$ wherein $R_5$ and $R_6$ are independently hydrogen, methyl or acetyl.

3. The compound of claim 2 wherein $R'_1$ is $=O$.

4. The compound of claim 3 which is 4''-keto-avermectin B1a/B1b.

5. The compound of claim 3 which is 4''-keto-22,23-dihydro avermectin B1a/B1b.

6. The compound of claim 2 wherein $R'_1$ is $-NR_5R_6$ and $R_5$ and $R_6$ are independently hydrogen, methyl or acetyl.

7. The compound of claim 6 which is 4''-deoxy-4''-amino-avermectin B1a or B1b.

8. The compound of claim 6 which is 4"-deoxy-4"-amino-22,23-dihydro-avermectin Bla or Blb.

9. The compound of claim 6 which is 4"-deoxy-4"-acetylamino-avermectin Bla or Blb.

10. The compound of claim 6 which is 4"-deoxy-4"-acetylamino-22,23-dihydro avermectin Bla or Blb.

11. The compound of claim 6 which is 4"-deoxy-4"-N,N-dimethylamino-avermectin Bla or Blb.

12. The compound of claim 6 which is 4"-deoxy-4"-N,N-dimethylamino-22,23-dihydro avermectin Bla or Blb.

13. A method for the treatment of helminthiasis which comprises administering to an animal infected with helminths an effective amount of a compound of claim 1.

14. A composition useful for treating animals infected with helminths which comprises an inert carrier and an effective amount of a compound of claim 1.

* * * * *